United States Patent [19]

Blagg et al.

[11] Patent Number: 5,696,146
[45] Date of Patent: Dec. 9, 1997

[54] INDOLE DERIVATIVES AS STEROID 5α-REDUCTASE INHIBITORS

[75] Inventors: Julian Blagg; Graham Nigel Maw; David James Rawson, all of Sandwich, United Kingdom

[73] Assignee: Pfizer Inc., New York, N.Y.

[21] Appl. No.: 553,589

[22] PCT Filed: May 26, 1994

[86] PCT No.: PCT/EP94/01760

§ 371 Date: Nov. 16, 1995

§ 102(e) Date: Nov. 16, 1995

[87] PCT Pub. No.: WO94/27990

PCT Pub. Date: Dec. 8, 1994

[30] Foreign Application Priority Data

May 28, 1993 [GB] United Kingdom ............ 9311008
Aug. 20, 1993 [GB] United Kingdom ............ 9317529

[51] Int. Cl.⁶ .................. A61K 31/40; C07D 405/14; C07D 405/06
[52] U.S. Cl. .................. 514/414; 514/382; 548/253; 548/454
[58] Field of Search .................. 548/253, 454; 514/382, 414

[56] References Cited

FOREIGN PATENT DOCUMENTS 0458207 11/1991 European Pat. Off. .
9317014 9/1993 WIPO .
9505375 2/1995 WIPO .

*Primary Examiner*—Patricia L. Morris
*Attorney, Agent, or Firm*—Peter C. Richardson; Gregg C. Benson; James T. Jones

[57] ABSTRACT

Compounds of formula (I)

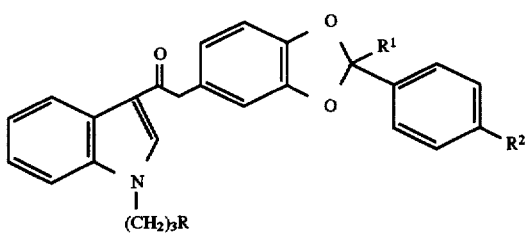

and the pharmaceutically acceptable base salts thereof, wherein R is $-CO_2H$ or tetrazol-5 yl; $R^1$ is $C_3-C_8$alkyl optionally substituted by fluoro; and $R^2$ is $C_2-C_4$alkyl, together with compositions containing, uses of, process for the preparation of, and intermediates used in the preparation of, such compounds. The compounds have steroid 5α-reductase inhibitory activity and are useful for treating a disease such as benign prostatic hypertrophy.

8 Claims, No Drawings

INDOLE DERIVATIVES AS STEROID 5α-REDUCTASE INHIBITORS

This is a National Phase filing under 35 USC §371 based on PCT/EP94/01760 which was filed internationally on May 26, 1994.

This invention relates to indole derivatives which have steroid 5α-reductase inhibitory activity.

More particularly this invention relates to certain 3-[(2, 2-disubstituted- 1,3-benzodioxolan-5-yl)methylcarbonyl] indole derivatives, their preparation and their use as testosterone 5α-reductase inhibitors.

The androgen class of steroidal hormones is responsible for the difference in the physical characteristics of males and females. Of all the organs that produce androgens, the tests produce these hormones in the greatest amounts. Overproduction of these hormones in the body results in many undesirable physical manifestations and disease states, e.g. acne vulgaris, alopecia, seborrhoea, females hirsutism, benign prostatic hypertrophy and male pattern baldness.

The principal androgen secreted by the testes is testosterone and it is the primary androgen present in male plasma. The principal mediators of androgenic activity in certain organs such as the prostate and sebaceous glands are the 5α-reduced androgens. Testosterone is therefore the prohormone of 5α-dihydrotestosterone which is formed locally in the above organs by the action of testosterone 5α-reductase, of which two isozymes are known to exist in humans, testosterone 5α-reductase-1 and testostemne 5α-reductase-2. The presence of elevated levels of dihydrotestosterone in many disease states has therefore focussed attention on the synthesis of testosterone 5α-reductase inhibitors.

Testosterone 5α-reductase inhibitors may also be useful in the treatment of human prostate adenocarcinomas.

Certain compounds of the present invention are generally disclosed by International Patent Publication No. WO 93/17014.

EP-A-0458207 discloses indole derivatives with testosterone 5α-reductase inhibitory activity.

It has now been surprisingly found that the present compounds are potent inhibitors of both isozymes of human testosterone 5α-reductase (i.e. 5α-reductase-1 and 5α-reductase-2) which leads to the therapeutic advantages that the compounds are more efficacious that they can be administered at lower doses.

The present invention provides compounds of the formula:

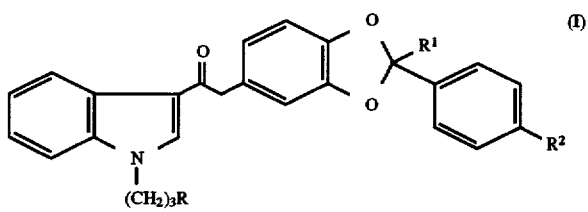

and the pharmaceutically acceptable base salts thereof, wherein

R is —$CO_2H$ or tetrazol-5-yl;

$R^1$ is $C_3$–$C_8$ alkyl optionally substituted by fluoro; and $R^2$ is $C_2$–$C_4$ alkyl.

Alkyl groups containing three or more carbon atoms may be straight-or branched-chain.

A compound of the formula (I) where R is —$CO_2H$ can be derived in vivo from a corresponding compound of the formula:

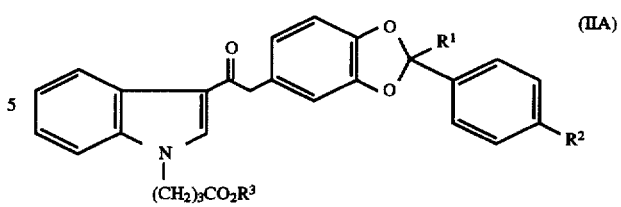

where $R^1$ and $R^2$ are as defined for a compound of the formula (I) and $R^3$ is a biolabile ester-forming group.

The term "biolabile ester-forming group" is well understood in medicinal chemistry as meaning a group which forms an ester which can be readily cleaved in vivo to liberate the corresponding compound of the formula (I) where R is —$CO_2H$. A number of such ester groups are well-known, for example in the penicillin area or in the case of the angiotensin-converting enzyme (ACE) inhibitor antihypertensive agents.

The compounds of the formula (IIA) are not only useful as pro-drugs to provide compounds of the formula (I) wherein R is —$CO_2H$ in vivo following oral administration, but are also useful as synthetic intermediates for the preparation of compounds of the formula (I) where R is —$CO_2H$.

The suitability of any particular ester-forming group for this purpose can be assessed by conventional in vitro or in vivo enzyme hydrolysis studies.

Examples of biolabile ester-forming groups are alkyl, alkanoyloxyalkyl (including alkyl, cycloalkyl or aryl substituted derivatives thereof), arylcarbonyloxyalkyl (including aryl substituted derivatives thereof), aryl, arylalkyl, indanyl and haloalkyl: wherein alkanoyl groups have from 2 to 8 carbon atoms, alkyl and haloalkyl groups have from 1 to 8 carbon atoms and aryl means phenyl or naphthyl, both of which may be optionally substituted by $C_1$–$C_4$ alkyl, $C_1$–$C_4$ alkoxy or halo. Alkyl, haloalkyl, alkanoyl and alkoxy groups can, where appropriate, be straight- or branched-chain.

Specific examples of biolabile ester-forming groups are $C_1$–$C_6$ alkyl (e.g. methyl, ethyl, n-propyl, isopropyl), benzyl, 1-(2,2-diethylbutyryloxy)ethyl, 2-ethylpropionyloxymethyl, 1-(2-ethylpropionyloxy)ethyl, 1-(2,4-dimethylbenzoyloxy)ethyl, α-benzoyloxybenzyl, 1-(benzoyloxy)ethyl, 2-methyl-1-propionyloxy-1-propyl, 2,4,6-trimethylbenzoyloxymethyl, 1-(2,4,6-trimethylbenzoyloxy)ethyl, pivaloyloxymethyl, phenethyl, phenpropyl, 2,2,2-trifluoroethyl, 1- or 2-naphthyl, 2,4-dimethylphenyl, 4-t-butylphenyl and 5-indanyl.

The pharmaceutically acceptable base salts of the compounds of the formula (I) are formed from suitable bases which form non-toxic salts and examples thereof are the aluminium, calcium, lithium, magnesium, potassium, sodium, zinc, N-benzyl-N-(2-phenylethyl)amine, 1-adamantylamine and diethanolamine salts.

Preferred base salts are the sodium, potassium, N-benzyl-N-(2-phenylethyl)amine and 1-adamantylamine salts.

For a review on suitable pharmaceutical salts see Berge et al, J. Pharm. Sci., 66, 1–19 (1977).

In the above definitions relating to the compounds of the formula (I):

Preferably R is —$CO_2H$.

Preferably $R^1$ is $C_3$–$C_8$ alkyl and more preferably is $C_3$–$C_6$ alkyl. Yet more preferably $R^1$ is n-propyl, n-butyl, n-pentyl or n-hexyl. Most preferably $R^1$ is n-butyl.

Preferably $R^2$ is $C_2$–$C_3$ alkyl. Most preferably $R^2$ is ethyl or n-propyl.

A compound of the formula (I) contains one or more asymmetric carbon atom(s) and therefore exists in two or more stereoisomeric forms. The present invention includes the individual stereoisomers of the compounds of the formula (I) and mixtures thereof, together, where appropriate, with all the tautomeric forms of the compounds of the formula (I). Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of a racemate using a suitable chiral support or by fractional crystallisation of the diastereoisomeric salts formed by reaction of a racemate with a suitable optically active base.

The preferred compounds of the formula (I) are 4-(3-[(2-n-butyl-2-[4-ethyl]phenyl-1,3-benzodioxolan-5-yl)methylcarbonyl]indol-1-yl)butanoic acid and 4-(3-[(2-n-butyl-2-[4-n-propyl]phenyl-1,3-benzodioxolan-5-yl)methylcarbonyl]indol-1-yl)butanoic acid, and the pharmaceutically acceptable base salts thereof.

The compounds of formula (I) provided by the invention may be prepared by the following methods:

1) The compounds of the formula (I) where R is —$CO_2H$ and $R^1$ and $R^2$ are as previously defined for a compound of the formula (I) may be prepared by cleavage of an ester of the formula:

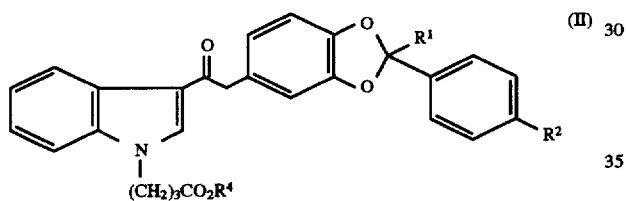

(II)

($CH_2)_3CO_2R^4$ where $R^4$ is a suitable ester-forming group that can be cleaved to provide a compound of the formula (I) where R is —$CO_2H$ and $R^1$ and $R^2$ are as previously defined for a compound of the formula (I).

A plethora of suitable ester-forming groups that may be cleaved to provide the corresponding carboxylic acid are known to the skilled person, see, e.g., T. W. Greene, "Protective Groups in Organic Synthesis", Wiley-Interscience (1981 ).

Where $R^4$ is an ester-forming group that may be removed by hydrolysis, e.g. a biolabile ester-forming group as previously defined for $R^3$ for a compound of the formula (IIA) (such as $C_1$–$C_6$ alkyl), the hydrolysis may be carried out under acidic or basic conditions, e.g. using an aqueous solution of either a suitable mineral acid or a suitable inorganic base. Preferably the hydrolysis is carried out under basic conditions.

In a typical hydrolysis procedure, an ester of the formula (II) is treated with an aqueous solution of a suitable base, e.g. sodium or potassium hydroxide, in the presence of a suitable organic co-solvent, e.g. 1,4-dioxane, tetrahydrofuran or a $C_1$–$C_4$ alkanol (e.g. methanol or ethanol) or a combination thereof. The hydrolysis is typically carried out at from room temperature to the reflux temperature and preferably at room temperature. The product is obtained as a base salt which may be converted to the carboxylic acid by acidification in the work-up procedure.

Where $R^4$ is an ester-forming group that may be removed by reduction, e.g. benzyl, the reduction may be carried out by catalytic hydrogenation using, e.g. palladium-on-charcoal, as the catalyst.

The compounds of the formula (II) (including the compounds of the formula (IIA)) may be prepared by esterification of a compound of the formula (I) where R is —$CO_2H$ with an alcohol of the formula $R^4OH$ (or $R^3OH$) where $R^4$ (or $R^3$) is as previously defined for this method.

The reaction may be carried out under classical esterification conditions such as by using an excess of the alcohol and with acid catalysis. e.g. using sulphuric acid or p-toluenesulphonic acid, at from room temperature to the reflux temperature. The water generated during the reaction may be removed by azeotropic distillation or by the use of a dehydrating agent or a molecular sieve.

The esterification may also be carried out by reacting the acid with the alcohol in the presence of a suitable dehydrating agent, e.g. dicyclohexylcarbodiimide or diethylazodicarboxylate/triphenylphosphine (see O. Mitsunobu, Synthesis, 1981, 1).

Alternatively the esterification may be carried out by first forming an activated ester or imidazolide derivative of the carboxylic acid, followed by reaction of the activated ester or imidazolide in situ with the alcohol of the formula $R^4OH$ (or $R^3OH$). An activated ester may be formed by reacting the carboxylic acid with 1-hydroxybenzotriazole in the presence of a suitable dehydrating agent, e.g. 1-(3-N,N-dimethylaminopropyl)-3-ethylcarbodiimide, and in a suitable solvent, e.g. dichloromethane, at room temperature. An imidazolide may be formed by reacting the carboxylic acid with 1,1'-carbonyldiimidazole in a suitable solvent, e.g. dichloromethane, at room temperature.

2) The compounds of the formula (I) where R is —$CO_2H$ and $R^1$ and $R^2$ are as previously defined for a compound of the formula (I) may be prepared by hydrolysis of a compound of the formula:

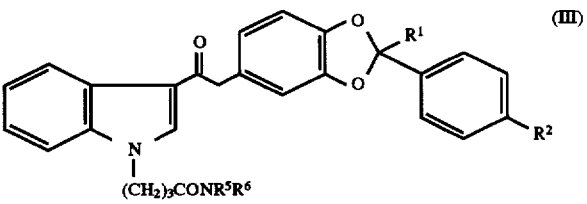

(III)

($CH_2)_3CONR^5R^6$ where $R^5$ and $R^6$ are each independently selected from H and $C_1$–$C_4$ alkyl and $R^1$ and $R^2$ are as previously defined for a compound of the formula (I).

The hydrolysis may be carried out under acidic or basic conditions, e.g. using an aqueous solution of either a suitable mineral acid (e.g. hydrochloric or sulphuric acid) or a suitable inorganic base (e.g. sodium or potassium hydroxide), at from room temperature to the reflux temperature. When basic hydrolysis conditions are used the product is obtained as a base salt which may be converted to the carboxylic acid by acidification in the work-up procedure.

3) The compounds of the formula (I) wherein R is —$CO_2H$ and $R^1$ and $R^2$ are as previously defined for a compound of the formula (I) may be prepared by hydrolysis of a compound of the formula:

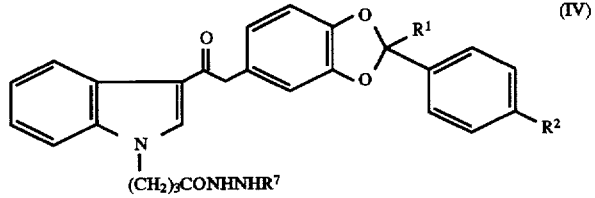

(IV)

where $R^1$ and $R^2$ are as previously defined for a compound of the formula (I) and $R^7$ is H or $C_1$–$C_4$ alkyl.

The hydrolysis may be carried out under acidic or basic conditions, e.g. using an aqueous solution of either a suitable acid (e.g. hydrochloric or acetic acid) or a suitable inorganic base (e.g. sodium or potassium hydroxide), at from room temperature to the reflux temperature. When basic hydrolysis conditions are used the product is obtained as a base salt which may be converted to the carboxylic acid by acidification in the work-up procedure.

4) The compounds of the formula (I) where R is —$CO_2H$ and $R^1$ and $R^2$ are as previously defined for a compound of the formula (I) may be prepared by hydrolysis of a compound of the formula:

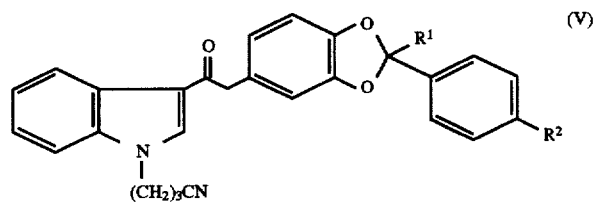

(V)

where $R^1$ and $R^2$ are as previously defined for a compound of the formula (I).

The hydrolysis may be carried out under acidic or basic conditions, e.g. using an aqueous solution of either a suitable acid (e.g. hydrochloric or sulphuric acid) or a suitable inorganic base (e.g. sodium or potassium hydroxide), at from room temperature to the reflux temperature. When basic conditions are used hydrogen peroxide may optionally be present and also the product is obtained as a base salt which may be converted to the carboxylic acid by acidification in the work-up procedure.

5) The compounds of the formula (I) where R is —$CO_2H$ and $R^1$ and $R^2$ are as previously defined for a compound of the formula (I) may be prepared by acidic hydrolysis of a compound of the formula:

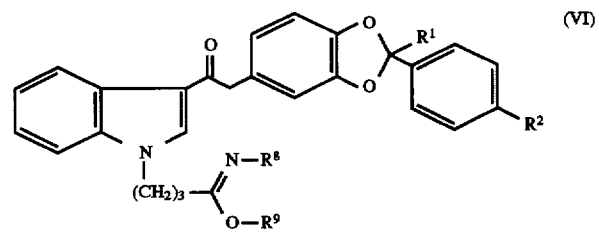

(VI)

where $R^1$ and $R^2$ are as previously defined for a compound of the formula (I) and $R^8$ and $R^9$ taken together represent ethylene, said ethylene being optionally substituted by phenyl or $C_1$–$C_4$ alkyl (preferably methyl). Preferably $R^8$ and $R^9$ taken together represent —$CH_2$ $C(CH_3)_2$—.

The hydrolysis may be carried out using an aqueous solution of a suitable acid such as hydrochloric acid at from room temperature to the reflux temperature.

6) All the compounds of the formula (I) may be prepared by alkylation of a base salt (i.e. the N-deprotonated form) of a compound of the formula:

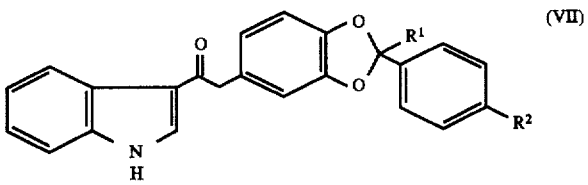

(VII)

where $R^1$ and $R^2$ are as previously defined for a compound of the formula (I), with a compound of the formula:

(VIII)

or a base salt thereof, or with a base salt of a compound of the formula $Z(CH_2)_3$—$CO_2H$, where Z is a suitable leaving group, e.g. halo (preferably bromo or iodo), methanesulphonyloxy or p-toluenesulphonyloxy.

The preferred base salts of the compounds of the formula $Z(CH_2)_3$—$CO_2H$ include the alkali metal and alkaline earth metal salts, e.g. the sodium and potassium salts.

The preferred base salts of the compounds of the formulae (VII) and (VIII) include the alkali metal salts, e.g. the sodium and potassium salts.

The reaction may be performed by initial deprotonation of a compound of the formula (VII) with a suitable base, e.g. sodium hydride or potassium carbonate, followed by reaction of the resulting anion with a compound of the formula (VIII) or a base salt thereof, or with a base salt of a compound of the formula $Z(CH_2)_3CO_2H$, as appropriate. The reaction may be carried out in a suitable solvent, e.g. N,N-dimethylformamide, tetrahydrofuran or 2-butanone, at from 0° C. to the reflux temperature.

Alternatively the reaction may be carried out under phase transfer conditions using a suitable base such as sodium or potassium hydroxide.

The compound of the formula (I) may be obtained as a base salt which can be converted to the carboxylic acid or NH-tetrazole, as appropriate, by acidification in the work-up procedure.

7) The compounds of the formula (I) where R is —$CO_2H$ and $R^1$ and $R^2$ are as previously defined for a compound of the formula (I) may be prepared by oxidative cleavage of a compound of the formula:

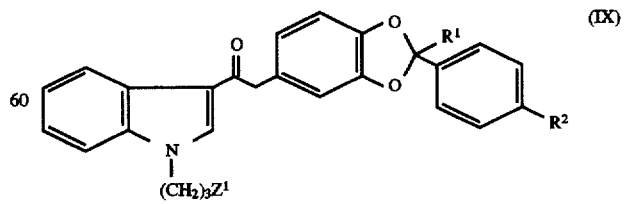

(IX)

where $Z^1$ is —CH=$CH_2$ or —C≡CH and $R^1$ and $R^2$ are as previously defined for a compound of the formula (I).

The reaction may be carried out by ozonolysis or by treatment with aqueous potassium permanganate solution.

8) The compounds of the formula (I) wherein R is —CO$_2$H and R$^1$ and R$^2$ are as previously defined for a compound of the formula (I) may be prepared by oxidation of a compound of the formula:

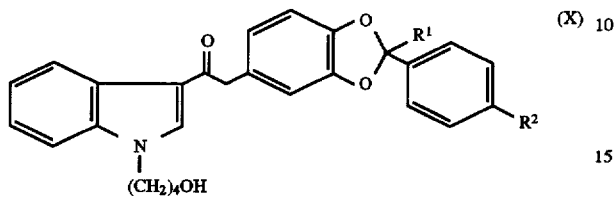
(X)

where R$^1$ and R$^2$ are as previously defined for a compound of the formula (I). A suitable oxidising agent for this purpose is chromium trioxide in pyridine.

9) All the compounds of the formula (I) may be prepared by reaction of a compound of the formula:

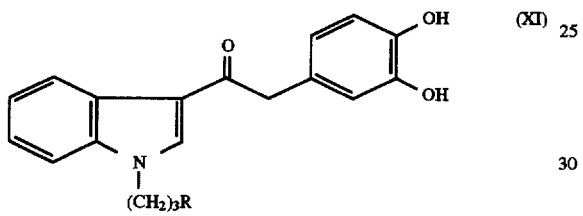
(XI)

where R is as previously defined for a compound of the formula (I), with a) a compound of the formula:

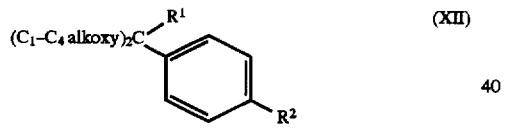
(XII)

where R$^1$ and R$^2$ are as previously defined for a compound of the formula (I). In a typical procedure the ketal of the formula (XII) and the compound of the formula (XI) are heated together under reflux in a suitable organic solvent, e.g. toluene, in the presence of a catalytic amount of a suitable acid, e.g. p-toluenesulphonic acid. Preferably a dimethyl ketal is used and the reaction is carried out in a Dean-Stark apparatus;

b) a compound of the formula:

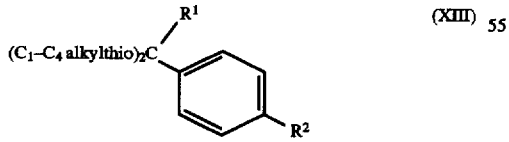
(XIII)

where R$^1$ and R$^2$ are as previously defined for a compound of the formula (I). The preferred C$_1$–C$_4$ alkyl group in the compounds of the formula (XIII) is methyl. In a typical procedure the compounds of the formula (XI) and (XIII) are heated together in a suitable organic solvent, e.g. toluene, with mercury (11) catalysis, e.g. using mercury (11) chloride;

c) a compound of the formula:

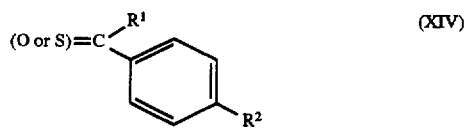
(XIV)

where R$^1$ and R$^2$ are as previously defined for a compound of the formula (I). In a typical procedure the compounds of the formulae (XI) and (XIV) are heated together under reflux in a suitable organic solvent, e.g. toluene, in the presence of a suitable acid catalyst, e.g. hydrochloric acid or sulphuric acid, and preferably in a Dean-Stark apparatus; or, d) for compounds of the formula (I) where the R$^1$ moiety has a hydrogen atom on the α-carbon atom with respect to its position of attachment to the 1,3-benzodioxolane ring, an enol ether derivative of a compound of the formula:

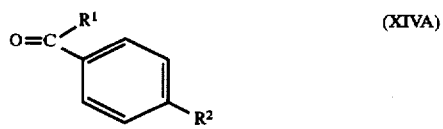
(XIVA)

where R$^1$ and R$^2$ are as previously defined for a compound of the formula (I) but with the above condition applying in respect of the definition of R$^1$. The reaction is typically carried out in a suitable organic solvent, e.g. toluene, in the presence of an acid catalyst, e.g. p-toluenesulphonic, hydrochloric or sulphuric acid, at from room temperature to the reflux temperature of the solvent.

Suitable enol ether derivatives for use in this procedure (d) may be derived from a compound of the formula (XIVA) by reaction with a suitable tri(C$_1$–C$_4$ alkyl) orthoformate, e.g. trimethyl orthoformate, in the presence of an acid catalyst, e.g. p-toluenesulphonic acid.

To prepare a compound of the formula (I) any one of methods (9)(a) to (d) may also be carried out using a suitable base (e.g. sodium) salt of a compound of the formula (XI), e.g. where R is —CO$_2$H, a carboxylate salt, the reaction being followed by an acidification step in the work-up procedure, as appropriate. The starting materials of the formula (XI) may be prepared by acidic hydrolysis of a compound of the formula:

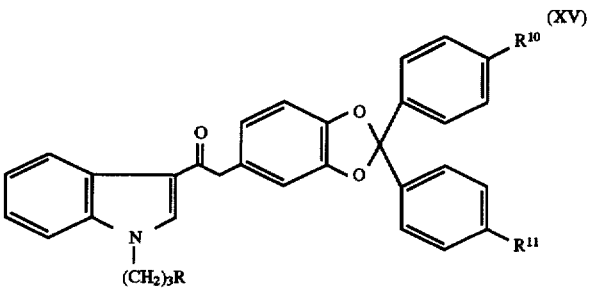
(XV)

where R$^{10}$ and R$^{11}$ are each independently selected from H and Cl and are preferably both Cl, and R is as previously defined for a compound of the formula (I). In a typical procedure the hydrolysis is carried out using aqueous acetic acid and the reaction is heated under reflux.

The compounds of the formula (XV) may be prepared by similar methods to those described herein for the preparation of the compounds of the formula (I).

10) The compounds of the formula (I) where R is tetrazol-5-yl and $R^1$ and $R^2$ are as previously defined for a compound of the formula (I), may be prepared by reaction of a compound of the formula (V) where $R^1$ and $R^2$ are as previously defined for a compound of the formula (I), with a suitable azide, e.g. an alkali metal azide (preferably sodium azide) or trimethylsilylazide in the presence of fluoride ion. The reaction is typically carried out in a suitable solvent, e.g. N-methyl-2-pyrrolidinone, at from 100° to 150° C. (see Synthesis, 1987, 1133).

11) The compounds of the formula (I) where R is tetrazol-5-yl and $R^1$ and $R^2$ are as previously defined for a compound of the formula (I), may be prepared by deprotection of a compound of the formula:

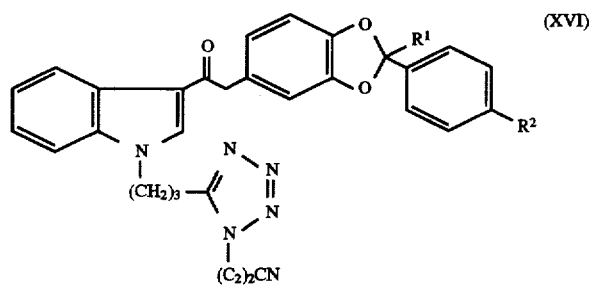

(XVI)

where $R^1$ and $R^2$ are as previously defined for a compound of the formula (I).

In a typical procedure the deprotection is carried out using a suitable base, e.g. sodium hydroxide, and in a suitable solvent, e.g. tetrahydrofuran/methanol, at about room temperature.

A compound of the formula (XVI) may be prepared by a two-step procedure starting from the corresponding compound of the formula (I) where R is —$CO_2H$ and $R^1$ and $R^2$ are as previously defined for a compound of the formula (I). In the first step the carboxylic acid is reacted with 3-aminopropanitrile under standard peptide coupling conditions, e.g. using 1-(3-N,N-dimethylaminopropyl)-3-ethylcarbodiimide and 1-hydroxybenzotriazole in a suitable solvent such as dichloromethane, to provide a compound of the formula:

(XVII)

where $R^1$ and $R^2$ are as previously defined for a compound of the formula (I).

A compound of the formula (XVII) may be converted to a compound of the formula (XVI) by treatment with trimethylsilylazide, diethylazodicarboxylate and triphenylphosphine in a suitable solvent, e.g. tetrahydrofuran, at room temperature.

This method of converting a compound of the formula (I) where R is —$CO_2H$ to a compound of the formula (I) where R is tetrazol-5-yl is based on a literature procedure that is described in J. Org. Chem., 56, 2395 (1991).

The compounds of the formulae (II), (IIA), (III), (IV), (V), (VI), (IX), (X), (XV), (XVI) and (XVII) can all be prepared by appropriate alkylation of a base salt of a compound of the formula (VII) by a similar procedure to that described in method (6) for the preparation of the compounds of the formula (I).

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable base salt of a compound of the formula (I) may be readily prepared by mixing together solutions of a compound of the formula (I) and the desired base. The salt may precipitate from solution and be collected by filtration or may be recovered by evaporation of the solvent.

The compounds of the formula (I) are steroid 5α-reductase inhibitors and therefore they are useful in the treatment of diseases or conditions such as acne vulgaris, alopecia, seborrhoea, female hirsutism, benign prostatic hypertrophy and male pattern baldness.

The compounds of the formula (I) are also useful for the treatment of human prostate adenocarcinomas.

The compounds of the formula (I) may be tested in vitro for testosterone 5α-reductase inhibitory activity as follows:

(1) The compounds of the formula (I) may be tested for their potency in inhibiting rat testosterone 5α-reductase using ventral prostate tissue from male rats. In determining inhibitory potency against rat prostatic 5α-reductase the following procedure was employed:

Rat prostates were minced into small pieces. The tissue was homogenised in Buffer A (20 mM sodium phosphate, pH 6.5, buffer containing 0.32M sucrose and 1 mM dithiothreitol) with a Brinkman Polytron (Kinematica GmBH, Luzern), and then homogenised with a motor-driven (1000 rpm) Potter Elvehjem (teflon-to-glass) homogeniser. Prostate particles were obtained by centrifugation at 105,000G for 60 minutes. The pellet was washed in 4 volumes of Buffer A and recentrifuged at 105,000G. The resulting pellet was dispersed in Buffer A (1 ml per g of prostate tissue originally used) with a motor-driven Potter Elvehjem homogeniser as described above. The particulate suspension was stored as 1 ml samples at −70° C.

The following components, dissolved in Buffer B (40 mM sodium phosphate buffer, pH 6.5), were added to a test tube: 500 µl of [$^3$H]-testosterone (1 µCi, 1 nmol; Du Pont, NEN Research Products, Stevenage, U.K.), 100 µl of 0.5 mM NADPH, a compound of the formula (I) dissolved in 5 µl of dimethyl sulphoxide, and Buffer B to give a final reaction volume of 1 ml. The mixture was warmed to 37° C. and the reaction started by addition of an aliquot of prostate particulate suspension. The reaction mixture was incubated at 37° C. for 30 minutes and then quenched by addition with vigorous mixing of 2 ml of ethyl acetate containing 20 µg each of testosterone an 5α-dihydrotestosterone as carriers. The aqueous and organic layers were separated by centrifugation at 2000G for 10 minutes. The organic layer was transferred to a second test tube and evaporated to dryness under nitrogen. The residue was dissolved in 50–80 µl of absolute ethanol, spotted onto a silica gel 60 F254 TLC plate (E. Merck, Darmstadt, Germany) and developed in dichloromethane:acetone (185:15).

The radiochemical content in the bands of the substrate (testosterone) and the product (5α-dihydrotestosterone)

were determined with a RITA Radio TLC Analyser (Raytest Instruments Ltd., Sheffield, U.K.). The percent of recovered radiolabel converted to 5α-dihydrotestosterone was calculated and used to determine enzyme activity. All incubations were conducted so that no more than 15% of substrate (testosterone) was converted to product.

The experimentally obtained data for a range of inhibitor concentrations was computer fitted to a sigmoidal dose-response curve and concentrations of compound giving 50% inhibition of 5α-reductase activity ($IC_{50}$'s) were calculated using a SIGFIT program (De Lean, A., Munson, P. J. and Rodbard, D., American Journal of Physiology, 235, E97 (1978)).

(2) The compounds of the formula (I) may be tested for their potency in inhibiting human testosterone 5α-reductase-2 using tissue from hyperplastic human prostates. In determining inhibitory potency against human prostatic 5α-reductase-2 the following procedure was employed:

Frozen human prostate tissue was pulverised in liquid nitrogen using a steel mortar and pestle. The powdered tissue was homogenised in 4 volumes of Buffer A (20 mM sodium phosphate, pH 6.5, containing 0.32M sucrose, 1 mM dithiothreitol and 50 μM NADPH) with an Ultra-Turrax homogeniser (Janke and Kunkel GmBH & Co., Staufen i. BR., Germany). The homogenate was centrifuged at 500G for 5 minutes to remove large particles of tissue, and the supernatant was then centrifuged at 100,000G for 1 hour. The resulting pellet was dispersed in Buffer A (1 ml per g of prostate tissue originally used) with the Ultra-Turrax homogeniser. This particulate preparation was then filtered through 2 layers of cheesecloth and the filtrate was stored as 2ml samples at −70° C.

The following components, dissolved in Buffer B (25 mM citrate phosphate buffer, pH 5.2), were added to a test tube: 100 μl of [$^3$H]-testosterone (1 μCi, 1 nmol; Du Pont, NEN Research Products, Stevenage, U.K.), 100 μl of NADPH regeneration system (5 mM NADPH, 50 mM glucose 6-phosphate, 5 units/ml glucose 6-phosphate dehydrogenase), a compound of the formula (I) dissolved in 5 μl of dimethyl sulphoxide, and Buffer B to give a final reaction volume of 1 ml. The mixture was warmed to 37° C. and the reaction started by addition of an aliquot of prostate particulate suspension. The reaction mixture was incubated at 37° C. for 30 minutes and was then quenched by addition, with vigorous mixing, of 2 ml of ethyl acetate containing 20 μg each of testosterone and 5α-dihydrotestosterone as carriers. The aqueous and organic layers were separated by centrifugation at 2000 G for 10 minutes. The organic layer was transferred to a second test tube and evaporated to dryness under nitrogen. The residue was dissolved in 50–80μl of absolute ethanol, spotted onto a silica gel 60 F254 TLC plate (E. Merck, Darmstadt, Germany) and developed in dichloromethane:acetone (185:15).

The radiochemical content in the bands of the substrate (testosterone) and the product (5α-dihydrotestosterone) were determined with a RITA Radio TLC Analyser (Raytest Instruments Ltd., Sheffield, U.K.). The percent of recovered radiolabel converted to 5α-dihydrotestosterone was calculated and used to determine enzyme activity. All incubations were conducted so that no more than 15% of substrate (testosterone) was converted to product.

The experimentally obtained data for a range of inhibitor concentrations was computer fitted to a sigmoidal dose-response curve and concentrations of compound giving 50% inhibition of 5α-reductase activity ($IC_{50}$'s) were calculated using a SIGFIT program (De Lean, A., Munson, P. J. and Rodbard, D., American Journal of Physiology, 235, E97 (1978)).

(3) The compounds of the formula (I) may be tested for potency in inhibiting steroid 5α-reductase activity in human prostate adenocarcinomas using cell lines DU145and HPC36M. In determining inhibitory potency against steroid 5α-reductase the following procedure was employed:

Human prostate adenocarcinoma cell lines were grown in Dulbecco's Modified Eagles medium (DMEM) containing 5% serum. The cells were recovered from the medium by centrifugation, washed in serum-free DMEM and suspended at 5–10×10$^6$ cells/mi. in serum-free medium.

The following components were added to a test tube: 10 μl of [$^3$H]-testosterone (1 μCi, 20 pmol) dissolved in ethanol (Du Pont, NEN Research Products, Stevenage, U.K.) and 5 μl of an ethanol solution of a compound of the formula (I). The ethanol was evaporated under nitrogen and the testosterone and the compound were redissolved in 0.25 ml of serum-free medium containing 0.25 μmol NADPH. The mixture was warmed to 37° C. and the reaction started by addition of 0.25 ml of cell suspension (1.2–2.5×10$^6$ cells). The reaction mixture was incubated at 37° C. for 2 hours and then quenched by addition, with vigorous mixing, of 1.5 ml of ethyl acetate containing 20 μg each of testosterone and 5α-dihydrotestosterone as carriers.

The aqueous and organic layers were separated by centrifugation at 2000 G for 10 minutes. The organic layer, containing testosterone and its metabolites, was transferred to a second test tube and evaporated to dryness under nitrogen. The residue was dissolved in 50–80 μl of absolute ethanol, spotted onto a silica gel 60 F254 TLC plate (E. Merck, Darmstadt, Germany) and developed in dichloromethane: acetone (185:15).

The radiochemical content in the bands of the substrate (testosterone) and the product (5 α-dihydrotestosterone) was determined with a RITA Radio TLC Analyser (Raytest Instruments Ltd., Sheffield, U.K.). The percentage of recovered radiolabel converted to 5α-dihydrotestosterone was calculated and used to determine enzyme activity. All incubations were conducted so that no more than 15% of substrate (testosterone) was converted to product.

The experimentally obtained data for a range of inhibitor concentrations was computer fitted to a sigmoidal dose-response curve and concentrations of compound giving 50% inhibition of 5α-reductase activity ($IC_{50}$'s) were calculated using a SIGFIT program (De Lean, A., Munson, P. J. and Rodbard D., American Journal of Physiology, 235, E97 (1978)).

(4) The compounds of the formula (I) may be tested in vitro for human testosterone 5α-reductase-1 inhibitory activity using cloned human testosterone 5α-reductase-1 according to the procedure described in Proc. Natl. Acad. Sci. USA, 87, 3640 (1990).

For human use, the compounds of the formula (I) can be administered alone, but will generally be administered in admixture with a pharmaceutical diluent or carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) will be from 0.01 to 20 mg/kg (in single or divided doses) and preferably will be from 0.1 to 10 mg/kg except for the treatment of human prostate adenocarcinomas where doses of up to 20 mg/kg may be used. Thus tablets or capsules of the compounds will contain from 5mg to 0.5g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) may also be administered together with an α-antagonist (e.g. prazosin or doxazosin), an antiandrogen (e.g. flutamide) or an aromatase inhibitor (e.g. atamestane), particularly for the treatment of benign prostatic hypertrophy.

It is to be appreciated that reference to treatment includes prophylaxis as well as the alleviation of established symptoms of the disease.

Thus the invention further provides:

i) a pharmaceutical composition comprising a compound of the formula (I), or a pharmaceutically acceptable base salt thereof, together with a pharmaceutically acceptable diluent or carrier;

ii) a compound of the formula (I), or a pharmaceutically acceptable base salt or composition thereof, for use as a medicament;

iii) the use of a compound of the formula (I), or of a pharmaceutically acceptable base salt or composition thereof, for the manufacture of a medicament for inhibiting asteroid 5α-reductase;

iv) the use of a compound of the formula (I), or of a pharmaceutically acceptable base salt or composition thereof, for the manufacture of a medicament for the treatment of acne vulgaris, alopecia, seborrhoea, female hirsutism, benign prostatic hypertrophy, male pattern baldness or a human prostate adenocarcinoma;

v) a method of treatment of a human to inhibit asteroid 5α-reductase which comprises treating said human with an effective amount of a compound of the formula (I) or with a pharmaceutically acceptable base salt or composition thereof;

vi) a method of treatment of a human to treat acne vulgaris, alopecia, seborrhoea, female hirsutism, benign prostatic hypertrophy, male pattern baldness or a human prostate adenocarcinoma which comprises treating said human with an effective amount of a compound of the formula (I) or with a pharmaceutically acceptable base salt or composition thereof; and vii) a compound of the formula (II), (III), (IV), (V), (VI), (VII) or a base salt thereof, (IX), (X) or (XI) or a base salt thereof.

The following Examples illustrate the preparation of the compounds of the formula (I):

EXAMPLE 1

4-(3-[(2-n-Butyl-2-[4-n-propyl]phenyl-1,3-benzodioxolan-5-yl)methylcarbonyl]indol-1-yl) butanoic acid

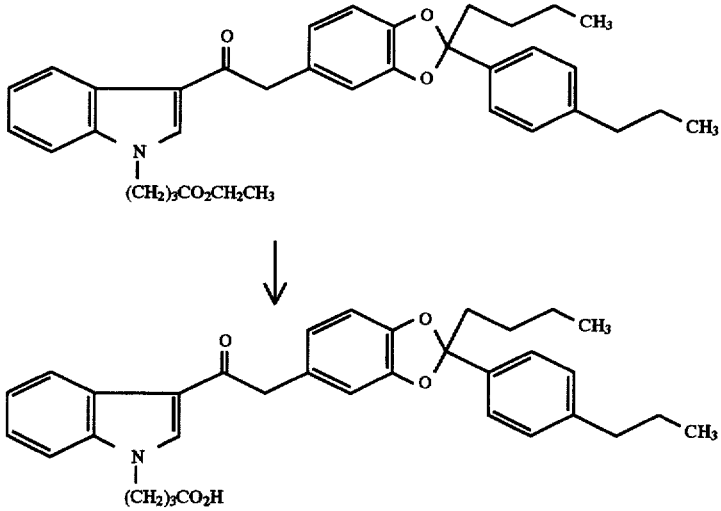

A suspension of ethyl 4-(3-[(2-n-butyl-2-[4-n-propyl] phenyl-1,3-benzodioxolan-5-yl)methylcarbonyl]indol-1-yl) butanoate (536 mg) (see Preparation 1) in tetrahydrofuran (10 ml) and methanol (20 ml) was treated with 2N aqueous sodium hydroxide (10 ml) and stirred for one hour at 20° C. The solution was acidified with 2N aqueous hydrochloric acid, extracted with ethyl acetate and the organic phase dried with magnesium sulphate. Filtration and concentration of the filtrate gave the title compound as a white foam (400 mg). Found: C, 75.59; H, 7.02; N, 2.59. $C_{34}H_{37}NO_5$ requires: C,75.67; H, 6.91; N, 2.60%. LRMS m/z=541 (m+1)$^+$.

$^1$H-NMR (CDCl$_3$): δ=0.88(t,3H), 0.92(t,3H), 1.20–1.48 (m,6H), 1.55–1.65 (m,2H), 2.15–2.25(m,4H), 2.39(t,2H), 2.58(t,2H), 4.05(s,2H), 4.20(t,2H), 6.75(s,2H), 6.80(s, 1H), 7.25(d,2H), 7.28–7.40(m,3H), 7.42(d,2H), 7.78(s, 1H), 8.40 (m, 1H) ppm.

EXAMPLE 2

4-(3-[(2-n-Hexyl-2-[4-n-propyl[phenyl-1,3-benzodioxolan-5-yl)methylcarbonyl]indol-1-yl) butanoic acid

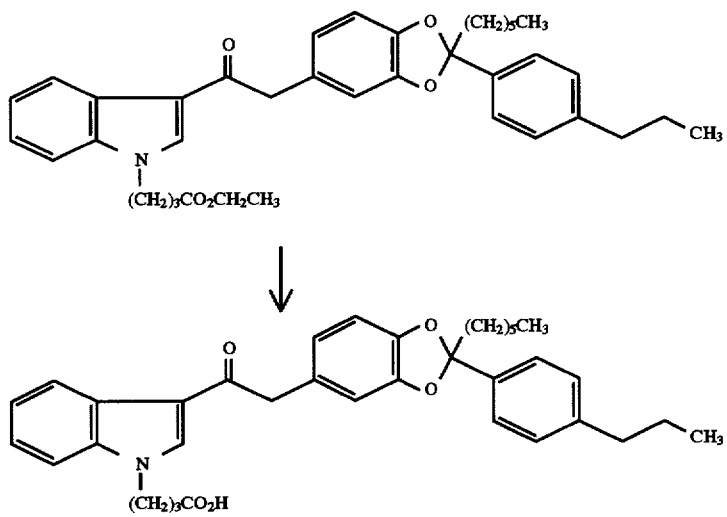

The title compound was prepared by a similar procedure to that of Example 1 using ethyl 4-(3-[(2-n-hexyl-2-[4-n-propyl]phenyl-1,3-benzodioxolan-5-yl)methylcarbonyl] indol-1-yl)butanoate (see Preparation 2) as the starting material. The compound was obtained as a white foam. Found: C, 76.28; H, 7.33; N, 2.64. $C_{36}H_{41}NO_5$ requires: C, 76.16; H, 7.28; N,2.47%. LRMS m/z=569(m+1)$^+$.

$^1$H-NMR (CDCl$_3$): δ=0.85(t,3H), 0.95(t,3H), 1.20–1.38 (m,8H), 1.50–1.68(m,2H), 2.15–2.25(m,4H), 2.38(t,2H), 2.47(t,2H), 4.00(s,2H), 4.22(t,2H), 6.70(s,2H), 6.80(s,1H), 7.15(d,2H), 7.28–7.39(m,3H), 7.40(d,2H), 7.75(s, 1H), 8.40 (m,1H) ppm.

EXAMPLES 3 to 6

The compounds of the following tabulated Examples of the general formula:

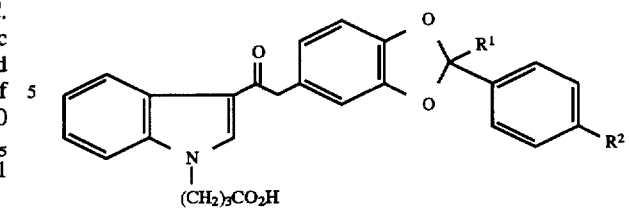

were prepared by similar procedures to that of Example 1 using the corresponding esters (see Preparations 14 to 17) as the starting materials.

| Example No. | R$^1$ | R$^2$ | LRMS (m/z) | Analysis/$^1$H-NMR/ Optical Rotation |
|---|---|---|---|---|
| 3 | n-propyl | n-propyl | 526 (m+1)$^+$ | $^1$H-NMR(CDCl$_3$): δ=0.90(t, 3H), 0.92(t, 3H), 1.35–1.50(m, 2H), 1.55–1.65(m, 2H), 2.12–2.28(m, 4H), 2.38(t, 2H), 2.55(t, 2H), 4.04(s, 2H), 4.25(t, 2H), 6.72(s, 2H), 6.80(s, 1H), 7.15(d, 2H), 7.30–7.48(m, 5H), 7.78(s, 1H), 8.40(m, 1H)ppm. |
| 4 | n-pentyl | n-propyl | 554 (m+1)$^+$ | Found: C, 75.32; H, 7.23; N, 2.36. $C_{35}H_{39}NO_5$ requires: C, 75.92; H, 7.10; N, 2.53%. $^1$H-NMR(CDCl$_3$): δ=0.85(t, 3H), 0.95(t, 3H), 1.20–1.32(m, 4H), 1.35–1.50(m, 2H), 2.10–2.25(m, 2H), 2.36(t, 2H), 2.56(t, 3H), 4.05(s, 2H), 4.25(t, 2H), 6.70(s, 2H), 6.80(s, 1H), 7.15(d, 2H), 7.30–7.50(m, 5H), 7.78(s, 1H), 8.40(m, 1H)ppm. |
| 5 | n-butyl | ethyl | 526 (m+1)$^+$ | Found: C, 74.24; H, 6.54; N, 2.40. $C_{33}H_{35}NO_5$.0.50 H$_2$O requires: C, 74.13; H, 6.79; N, 2.62%. $^1$H-NMR(CDCl$_3$): δ=0.85(t, 3H), |

-continued

| Example No. | $R^1$ | $R^2$ | LRMS (m/z) | Analysis/$^1$H-NMR/Optical Rotation |
|---|---|---|---|---|
| | | | | 1.20(t, 3H), 1.25–1.45(m, 6H), 2.12–2.25(m, 4H), 2.35(t, 2H), 2.60(q, 2H), 4.00(s, 2H), 4.25(t, 2H), 6.75(s, 2H), 6.80(s, 1H), 7.20(d, 2H), 7.25–7.48(m, 5H), 7.75(s, 1H), 8.40(m, 1H)ppm. |
| 6[1] | n-butyl | n-propyl | 541 (m+1)⁺ | Found: C, 75.23; H, 6.81; N, 2.30. $C_{34}H_{37}NO_5$ requires: C, 75.67; H, 6.91; N, 2.60%. $^1$H-NMR(CDCl$_3$): Identical in all respects to that obtained for the racemic compound of Example 1. $[\alpha]_D^{25}$ +62°(c=0.1, methanol). |

[1]The compound was obtained as a single enantiomer using Enantiomer A from Preparation 17 as the starting material.

EXAMPLE 7

4-(3-[(2-n-Butyl-2-[4-ethyl ]phenyl-1,3-benzodioxolan-5-yl)methylcarbonyl]indol-1-yl butanoic acid, enantiomer A

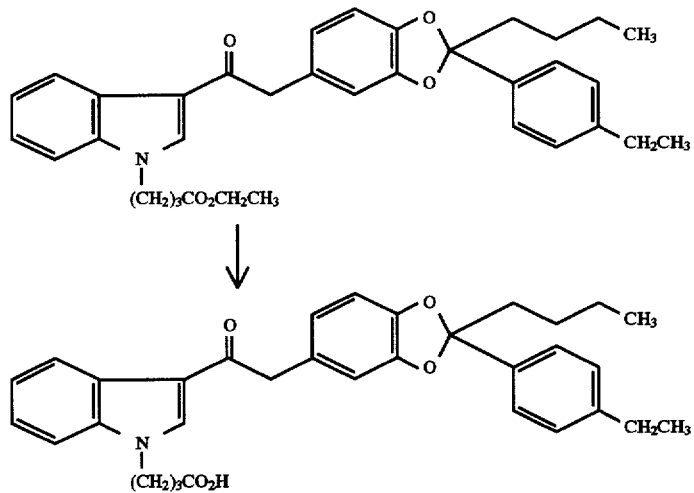

The title compound was prepared by a similar method to that of Example 1 using ethyl 4-(3-[(2-n-butyl-2-[4-ethyl]phenyl-1,3-benzodioxolan-5-yl)methylcarbonyl]indol-1-yl) butanoate, enantiomer A (see Preparation 18) as the starting material and 3:1 v/v 1,4-dioxane:water as the reaction solvent. The title compound was obtained in 90% enantiomeric excess as a foam. $[\alpha]^{20}_D$=+295° (c=1.0 mg/ml in methanol).

$^1$H-NMR(CDCl$_3$): Identical to that for Example 5.

Analytical HPLC (Chiralpak AD [trade mark] column, eluant=94:6 v/v hexane: isopropanol, flow rate=1 ml min$^{-1}$): R$_T$(Enantiomer B)=86.4 min., R$_T$(Enantiomer A)=93.0 min. Product obtained as a 95:5 mol/mol mixture of Enantiomer A: Enantiomer B.

The following Preparations illustrate methods for obtaining certain intermediates used in the preparation of the compounds of the preceding Examples:

PREPARATION 1

Ethyl 4-(3-[(2-n-butyl-2-]4-n-propyl]phenyl-1,3-benzodioxolan-5-yl)methylcarbonyl]indol-1-yl) butanoate

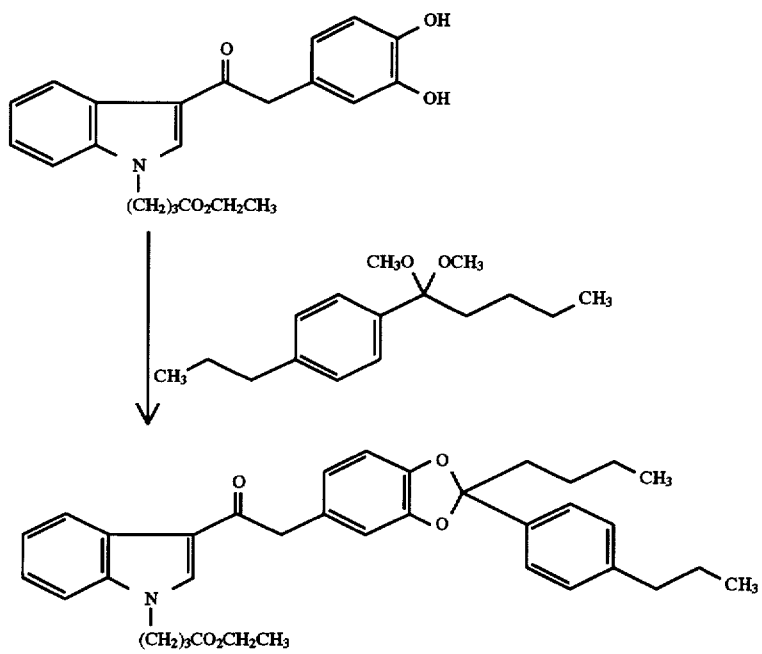

A mixture of 1,1-dimethoxy-1-(4-n-propyl) phenylpentane (520 mg) (see Preparation 3) and ethyl 4-(3-[(3,4-dihydroxyphenyl)methylcarbonyl]indol-1-yl) butanoate (400mg) (see Preparation 8) was suspended in toluene (30 ml) and heated under reflux for one hour in a Dean-Stark apparatus. The first few milliliters of toluene collected in the Dean-Stark trap were removed, the reaction was cooled to 60° C. and p-toluenesulphonic acid (25 mg) was added to the reaction mixture. The mixture was heated under reflux for 16 hours, cooled and triethylamine (0.5 ml) was added. The mixture was partitioned between diethyl ether (50 ml) and water (50 ml). The organic layer was separated and washed with 2N aqueous sodium hydroxide solution (20 ml) then brine (20 ml), and then dried (MgSO$_4$). Evaporation of the organic layer gave an oil which was purified by flash chromatography (silica, eluant=3:1 hexane/ ethyl acetate) to give the title compound as a yellow oil (550 mg).

LRMS m/z=568(m+1)$^+$.

$^1$H-NMR (CDCl$_3$): δ=0.85(t,3H), 0.95(t,3H), 1.25–1.50 (m,7H), 1.55–1.65(m,2H), 2.18–2.25(m,4H), 2.35(t,2H), 2.58(t,2H), 4.00(s,2H), 4.15(q,2H), 4.24(t,2H), 6.70(s,2H), 6.80(s,1H), 7.18(d,2H), 7.28–7.40(m,3H), 7.48(d,2H), 7.80 (s, 1H), 8.40(m, 1H) ppm.

PREPARATION 2

Ethyl 4-(3-[(2-n-hexyl-2-]4-n-propyl]phenyl-1,3-benzodioxolan,-5-yl)methylcarbonyl]indol-1-yl) butanoate The title compound was prepared by a similar method to that of Preparation 1 using 1,1-dimethoxy-1-(4-n-propyl) phenylheptane (see Preparation 4) as the ketal starting material. The compound was obtained as an oil. LRMS m/z=596(m+1)$^+$.

$^1$H-NMR (CDCl$_3$): δ=0.85(t,3H), 0.90(t,3H), 1.18–1.36 (m,11H), 1.55–1.65 (m,2H), 2.15–2.25(m,4H), 2.30 (t,2H), 2.60(t,2H), 4.00(s,2H), 4.15(q,2H), 4.25(t,2H), 6.70(s,2H), 6.80(s,1H), 7.15(d,2H), 7.28–7.40(m,3H), 7.40(d,2H), 7.78 (s,1H), 8.40(m,1H) ppm.

PREPARATION 3

1,1-Dimethoxy-1-(4-n-propyl)phenylpentane

A mixture of 1-(4-n-propyl)phenylpentan-1-one (500mg) (see Preparation 5), trimethyl orthoformate (1.1 ml), methanol (20 ml) and p-toluenesulphonic acid (10 mg) was heated under reflux for 16 hours. The cooled reaction mixture was basified (using a few drops of a 30% w/w solution of sodium methoxide in methanol) and the reaction mixture was partitioned between water (20 ml) and diethyl ether (20 ml). The ether layer was separated, washed with brine (20 ml) and dried (MgSO$_4$) to give the title compound as a colourless oil (600 mg).

$^1$H-NMR (CDCl$_3$): δ=1.80(t,3H), 0.90–1.02(m,5H), 1.10–1.25(m,2H), 1.60–1.75(m,2H), 1.85–1.92(m,2H), 2.60 (t,2H), 3.17(s,6H), 7.17(d,2H),7.36(d,2H) ppm.

PREPARATION 4

1,1-Dimethoxy-1-(4-n-propyl)phenylheptane

The title compound was prepared by a similar method to that of Preparation 3 using 1-(4-n-propyl)phenylheptan-1-one (see Preparation 6) as the ketone starting material. The compound was obtained as a colourless oil.

$^1$H-NMR (CDCl$_3$): δ=0.80(t,3H), 0.95(t,3H), 1.10–1.20 (m,8H), 1.60–1.70(m,2H), 1.80–1.95(m,2H), 2.60(t,2H), 3.15(s,6H), 7.15(d,2H), 7.36(d,2H) ppm.

PREPARATION 5

1-(4-n-Propyl)phenylpentan-1-one

A solution of n-butyl lithium (1.6N in hexane, 3.65 ml) in tetrahydrofuran (10 ml) was cooled to −78° C., treated dropwise with a solution of N-methoxy-N- methyl-4-n-propylbenzamide (1.1 g) (see Preparation 7) in tetrahydrofuran (10 ml) and the solution was allowed to warm to room temperature overnight. The reaction mixture was partitioned between dichloromethane (50 ml) and 2N aqueous hydrochloric acid (50 ml). The organic layer was separated, dried (MgSO$_4$) and evaporated to give a yellow oil which was subjected to flash chromatography (silica, eluant=3:1 hexane/ethyl acetate) to give the title compound as a clear oil (545 mg).

$^1$H-NMR (CDCl$_3$): δ=0.95(t,6H), 1.38–1.49(m,2H), 1.62–1.80(m,4H), 2.65(t,2H), 2.95(t,2H), 7.25(d,2H), 7.90 (d,2H) ppm.

PREPARATION 6

1-(4-n-Propyl)phenylheptan-1-one

A solution of 1-bromohexane (1.3 ml) in diethyl ether (25 ml) was added to magnesium turnings (330 mg). A gentle reflux was observed and the mixture was allowed to stir for one hour. The mixture was added dropwise to a cooled (−78° C.) solution of N-methoxy-N-methyl-4-n-propyl-benzamide (2.07 g) (see Preparation 7) in tetrahydrofuran (25 ml). The mixture was allowed to warm to room temperature overnight and then treated with saturated aqueous ammonium chloride solution (50 ml) and ethyl acetate (50 ml). The organic layer was separated, washed with 2N aqueous hydrochloric acid (50 ml), dried (MgSO$_4$) and evaporated to a yellow oil. Flash chromatography (silica, eluant=3:1 hexane/ethyl acetate) gave the title compound as a clear oil (970 mg). LRMS m/z=233(m+1)$^+$.

$^1$H-NMR (CDCl$_3$): δ=0.90(t,3H), 0.95(t,3H), 1.20–1.45 (m,6H), 1.60–1.80(m,4H), 2.65(t,2H), 2.95(t,2H), 7.15(d, 2H), 7.90(d,2H) ppm.

PREPARATION 7

N-Methoxy-N-methyl-4-n-propylbenzamide

A mixture of 4-n-propylbenzoic acid (10.0 g), 1-hydroxybenzotriazole hydrate (8.20 g), 1-(3-N,N-dimethylaminopropyl)-3-ethylcarbodiimide hydrochloride (21.5 g) and dichloromethane (1000 ml) was treated dropwise with triethylamine (42.6 ml) and N,O-dimethylhydroxylamine hydrochloride (6.6 g). The mixture was stirred overnight at room temperature and then treated with water (700 ml). The organic layer was separated, washed with 2N aqueous hydrochloric acid (4×500 ml) and then saturated aqueous sodium bicarbonate solution (4×500 ml). The organic phase was dried (MgSO$_4$) and concentrated to give the title compound as a clear oil (10.8 g).

$^1$H-NMR (CDCl3): δ=0.95(t,3H), 1.65(m,2H), 2.60(t, 2H), 3.36(s,3H), 3.58(s,3H), 7.20(d,2H), 7.60(d,2H) ppm.

PREPARATION 8

Ethyl 4-(3-[(3,4-dihydroxyphenyl)methylcarbonyl] indol-1-yl)butanoate

Ethyl 4-(3-[(2,2-di[4-chlorophenyl]-1,3-benzodioxolan-5-yl)methylcarbonyl]indol-1-yl)butanoate (9.5 g) (see Preparation 9) was dissolved in acetic acid/water (9:1) (100 ml) and heated under reflux for one hour. The reaction mixture was cooled, evaporated to dryness and partitioned between ethyl acetate and brine. The organic layer was separated, dried (MgSO$_4$) and evaporated to a brown oil. Flash chromatography (silica, eluant=10:1 dichloromethane/ ethanol) gave the title compound as a pale tan solid (4.5 g). LRMS m/z=382 (m+1)$^+$.

$^1$H-NMR (d$_6$-DMSO): δ=1.15(t,3H), 2.10(m,2H), 2.30(t, 2H), 3.90(s,2H), 4.00(q,2H), 4.25(t,2H), 6.55–6.60(m,2H), 6.70(s, 1H), 7.10–7.30(m,2H), 7.60(d,1H), 8.15(d,1H), 8.50 (s,1H) ppm.

PREPARATION 9

Ethyl 4-(3-[(2,2-di[4-chlorophenyl]-1,3-benzodioxolan-5-yl)methylcarbonyl]indol-1-yl) butanoate A suspension of 3-[(2,2-di[4-chlorophenyl]-1,3-benzodioxolan-5-yl)methylcarbonyl]-1H-indole (8.9 g) (see Preparation 10) in 2-butanone (200 ml) was treated with anhydrous potassium carbonate (12.2 g) and ethyl 4-bromobutanoate (5.2 g). The mixture was heated under reflux for 16 hours, filtered and evaporated. Flash chromatography (silica, eluant=dichloromethane) gave the title compound as a crystalline solid (9.68 g).

LRMS m/z=615(m+1)$^+$.

$^1$H-NMR (CDCl$_3$): δ=1.25(t,3H), 2.10–2.25(m,2H), 2.30 (t,2H), 4.02(s,2H), 4.10(q,2H), 4.23(t,2H), 6.80(m,2H), 6.85 (s,1H), 7.25–7.40(m,9H), 7.45(d,4H), 7.80(s, 1H), 8.40(m, 1H) ppm.

PREPARATION 10

3-](2,2-Di[4-chlorophenyl]-1,3-benzodioxolan-5-yl) methylcarbonyl]-1H-indole Methyl (2,2-di[4-chlorophenyl]-1,3-benzodioxolan-5-yl) acetate (13.7 g) (see Preparation 11) was dissolved in methanol (30 ml) and tetrahydrofuran (30 ml). A solution of sodium hydroxide (5.0 g) in water (20 ml) was added and the mixture was stirred for one hour at room temperature. The mixture was concentrated and the residue was partitioned between ethyl acetate and 5% aqueous citric acid. The organic layer was separated, washed with brine, dried (MgSO$_4$) and evaporated to provide the corresponding carboxylic acid as a white solid.

This material was dissolved in dichloromethane (200 ml), cooled to 0° C. and treated with oxalyl chloride (4.7 ml) and N,N-dimethylformamide (10 drops). After stirring at 0° C. for one hour the mixture was evaporated to dryness and was dissolved in toluene (30 ml) for use directly in the next step (see below).

Indole (7.72 g) was dissolved in toluene (50 ml), cooled to 0° C. and treated with methylmagnesium iodide (22 ml of a 3M solution in diethyl ether). The solution was cooled to −78° C. and treated with pyridine (5.2 g) followed by the solution of the acid chloride prepared as described above. After stirring overnight at room temperature, the mixture was treated with saturated aqueous ammonium chloride and ethyl acetate. The organic layer was separated, washed with brine, dried (MgSO$_4$) and evaporated to a gum. Trituration with 2:1 hexane/ethyl acetate (150 ml) gave the title compound as a pink solid (9.1 g). LRMS m/z=503(m)$^+$.

$^1$H-NMR (CDCl$_3$): δ=4.15(s,2H), 6.80(m,2H), 6.90(s, 1H), 7.30–7.50(m,11H), 7.90(m,1H), 8.40(m,1H), 8.60(s,br, 1H) ppm.

PREPARATION 11

Methyl(2,2-di[4-chlorophenyl]-1,3-benzodioxolan-5-yl)acetate

A mixture of di(4-chlorophenyl)dimethoxymethane (26 g) (see Preparation 13) and methyl (3,4-dihydroxyphenyl) acetate (16 g) (see Preparation 12) in toluene (200 ml) was heated under reflux in a Dean-Stark apparatus for one hour. The reaction was cooled to 60° C. and p-toluenesulphonic acid was added (50 mg). After heating under reflux for 16 hours the solution was cooled, washed with aqueous sodium bicarbonate (100 ml), dried (MgSO₄) and evaporated to a brown gum. Flash chromatography (silica, eluant=4:1 hexane/ethyl acetate) gave the title compound as a pale yellow gum (13.7 g). LRMS m/z=415(m)⁺.

¹H-NMR (CDCl₃): δ=3.50(s,2H), 3.65(s,3H), 6.70–6.85 (m,3H), 7.30(d,4H), 7.48(d,4H) ppm.

PREPARATION 12

Methyl (3,4-dihydroxyphenyl) acetate

A mixture of 3,4-dihydroxyphenylacetic acid (10.0 g) and concentrated sulphuric acid (0.5 ml) in methanol (70 ml) was heated under reflux for 16 hours. The mixture was concentrated, water was added and the mixture was neutralised to pH7 using sodium carbonate. The cloudy solution obtained was extracted with dichloromethane (200 ml), dried (Na₂SO₄) and evaporated to give a yellow gum (7.64 g). LRMS m/z=183(m+1)⁺.

¹H-NMR (CDCl₃): δ=3.50(s,2H), 3.70(s,3H), 5.85(s,br, 1H), 6.15(s,br,1H), 6.65(d,2H), 7.75(m,2H) ppm.

PREPARATION 13

Di(4-chlorophenyl)dimethoxymethane

The title compound was prepared by a similar procedure to that of Preparation 3 using di(4-chlorophenyl) ketone as the ketone starting material. The compound was obtained as a white crystalline solid. LRMS m/z=268 (m-31)⁺.

¹H-NMR (CDCl₃): δ=3.10(s,6H), 7.25(d,2H), 7.45(d,2H) ppm.

PREPARATIONS 14 to 16

The compounds of the following tabulated Preparations of the general formula:

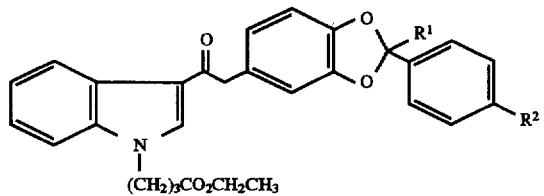

were prepared by similar procedures to that of Preparation 1 using the compound of Preparation 8 and the corresponding ketals (which were prepared by similar routes to those described in Preparations 3 to 7) as the starting materials.

| Preparation No. | R¹ | R² | LRMS (m/z) | ¹H-NMR |
|---|---|---|---|---|
| 14 | n-propyl | n-propyl | 554 (m+1)+ | ¹H-NMR(CDCl₃): δ=0.90(t, 3H), 0.92(t, 3H), 1.30(t, 3H), 1.35–1.50(m, 2H), 1.55–1.65(m, 2H), 2.15–2.28(m, 4H), 2.30(t, 2H), 2.55(t, 3H), 4.00(s, 2H), 4.18(q, 2H), 4.25(t, 2H), 6.72(s, 2H), 6.80(s, 1H), 7.15(d, 2H), 7.3–7.48(m, 5H), 7.78(s, 1H), 8.40(m, 1H)ppm. |
| 15 | n-pentyl | n-propyl | 582 (m+1)+ | ¹H-NMR(CDCl₃): δ=0.85(t, 3H), 0.95(t, 3H), 1.25(t, 3H), 1.20–1.32 (m, 4H), 1.35–1.50(m, 2H), 2.10–2.55(m, 2H), 2.36(t, 2H), 2.55(t, 2H), 4.05(s, 2H), 4.15(q, 2H), 4.25(t, 2H), |
| 16 | n-butyl | ethyl | 554 (m+1)+ | 6.70(s, 2H), 6.80(s, 1H), 7.15(d, 2H), 7.30–7.50(m, 5H), 7.80(s, 1H), 8.40(m, 1H)ppm. ¹H-NMR(CDCl₃): δ=0.85(t, 3H), 1.20(t, 3H), 1.25(t, 3H), 1.25–1.45 (m, 6H), 2.12–2.25(m, 4H), 2.35 (t, 2H), 2.60(q, 2H), 4.00(s, 2H), 4.15(q, 2H), 4.26(t, 2H), 6.80(s, 2H), 6.85(s, 1H), 7.20(d, 2H), 7.25–7.48 (m, 5H), 7.75(s, 1H), 8.40(m, 1H) ppm. |

PREPARATION 17

Resolution of ethyl 4-(3-[(2-n-butyl-2-[4-n-propyl]phenyl-1,3-benzodioxolan-5-yl)methylcarbonyl]indol-1-yl)butanoate The racemic compound of Preparation 1 was resolved into its component enantiomers by chromatography on a Chiralpak (trade mark) AD 25 cm preparative HPLC column using 9:1 v/v hexane:ethanol as the eluant at a flow rate of 1ml/min.

The fractions containing the first eluted enantiomer were combined and concentrated under reduced pressure to provide the title compound, Enantiomer A.

Analytical HPLC (Chiralpak AD, eluant=9:1 v/v hexane:ethanol, 1 ml/min.): R_T=14.48 min. (98.5% ee).

¹H-NMR and LRMS identical to that of the racemic compound of Preparation 1.

The later fractions were combined and concentrated under reduced pressure to provide the title compound, Enantiomer B, that was contaminated with the title compound, Enantiomer A.

Analytical HPLC (Chiralpak AD, eluant=9:1 v/v hexane:ethanol, 1ml/min.): R_T=21.06 min. (55.6% ee).

PREPARATION 18

Ethyl 4-(3-[(2-n-butyl-2-[4-ethyl]phenyl-1,3-benzodioxolan-5-yl)methylcarbonyl]indol-1-yl) butanoate, enantiomer A a) Methyl (2-n-butyl-2-[4-ethyl]phenyl-1,3-benzodioxolan-5-yl)acetate The title compound was prepared by a similar method to that of Preparation 11 using methyl (3,4-dihydroxyphenyl) acetate (see Preparation 12) and 1,1 -dimethoxy-1-(4-ethylphenyl)pentane (the ketal starting material of Preparation 16-prepared by a similar route to that described in Preparations 3, 5 and 7) as the starting materials. The title compound was obtained as a light orange oil.

¹H-NMR (CDCl₃): δ=0.80(t,3H), 1.20(t,3H), 1.20–1.40 (m,6H), 2.20(m,2H), 2.60(q,2H), 3.50(s,2H), 3.65(s,3H) ppm.

b) (2-n-Butyl-2-[4-ethyl]phenyl-1,3-benzodioxolan-5-yl) acetic acid, enantiomer A The ester of Preparation 18(a) was hydrolysed to provide the corresponding racemic carboxylic acid by a similar method to that of Preparation 10 except using aqueous 1,4-dioxane as the solvent for the reaction.

To a mixture of the above racemic carboxylic acid (16.5 g), ethyl acetate (82 ml) and acetone (82 ml) was added R-α-methylbenzylamine. The mixture was vigorously stirred for 30 minutes and left to stand overnight. The white crystalline material that formed was filtered off and recrystallised four times from 1:1 v/v ethyl acetate:acetone. The resulting material was dissolved in ethyl acetate (200 ml) and shaken with 1M aqueous hydrochloric acid solution (2×100 ml). The organic layer was dried (magnesium sulphate) and concentrated under reduced pressure to provide the title compound as an oil (2.95 g).

Analytical HPLC (Chiralpak AD [trade mark] column eluting with 98:2:0.1 by volume hexane:isopropanol:trifluoroacetic acid at a flow rate of 1 ml min$^{-1}$): retention time=14.76 min., 90% ee.

LRMS m/z=341(m+1)$^+$ $^1$H-NMR(CDCl$_3$): δ=0.85(t,3H), 1.20(t,3H), 1.20–1.40 (m,4H), 2.20(t,2H), 2.65(q,3H), 3.50(s,2H), 6.60(d,1H), 6.70(d,2H), 7.15(d,2H), 7.40(d,2H) ppm.

(c) 3-[(2-n-Butyl-2-[4-ethyl]phenyl-1,3-benzodioxolan-5-yl)methylcarbonyl]-1H-indole, enantiomer A The title compound was prepared by first converting the compound of Preparation 18(b) to the corresponding acid chloride, followed by reaction of this acid chloride with indole by a similar method to that of Preparation 10. The title compound was obtained as an amorphous solid.

$^1$H-NMR(CDCl$_3$): δ=0.90(t,3H), 1.20(t,3H), 1.20–1.40 (m,6H), 2.20(t,2H), 2.60(q,2H), 4.00(s,2H), 6.70(s,2H), 6.75(s,1H), 7.05–7.40(m,7H), 7.80(d,1H), 8.40(m,1H), 8.60 (br. s,1H)ppm.

(d) Ethyl 4-(3-[(2-n-butyl-2-[4-ethyl]phenyl-1,3-benzodioxolan-5-yl)methylcarbonyl)indol-1-yl)butanoate, enantiomer A The title compound was prepared by a similar method to that of Preparation 9 using the compound of Preparation 18(c) and ethyl 4-bromobutanoate as the starting materials. The title compound was obtained as an oil.

$^1$H-NMR(CDCl$_3$): δ=0.90(t,3H), 1.10(t,3H), 1.20(t,3H), 1.20–1.40(m,6H), 2.15(m,4H), 2.30(t,2H), 2.60(q,2H), 4.00 (s,2H), 4.15(q,2H), 4.25(t,2H), 6.70(s,2H), 6.80(s, 1H), 7.15 (d,2H), 7.20–7.40(m,3H), 7.40(d,2H), 7.80(s,1H), 8.40(m, 1H)ppm.

COMPARATIVE DATA

The following Table shows the in vitro inhibitory activity of a selection of the compounds of the present Examples and the activity of the compound of Example 36 of WO 93/17014 against both cloned human testosterone 5α-reductase-1 and human testosterone 5α-reductase-2. The data were obtained using test method (4) set out on page 27 of the specification and test method (2) described on pages 24 to 26 of the specification, respectively.

It can be seen that, in contrast to the prior art compound, the present compounds show balanced, potent, inhibitory activity against both isozymes.

| Example No. | IC$_{50}$(nM) vs human testosterone 5α-reductase-1 | IC$_{50}$(nM) vs human testosterone 5α-reductase-2 |
| --- | --- | --- |
| 1 | 15.5 | 6.9 |
| 2 | 24.0 | 16.7 |
| 3 | 14.0 | 13.3 |
| 4 | 11.0 | 16.9 |
| 5 | 11.0 | 4.5 |
| 6 | 17.5 | 2.3 |
| Example 36 of PCT/EP93/00380 | 47.6 | 7.5 |

We claim:

1. A compound of the formula:

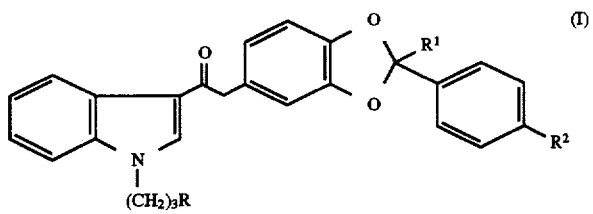

or a pharmaceutically acceptable base salt thereof, wherein
R is —CO$_2$H or tetrazol-5-yl;
R$^1$ is C$_3$–C$_8$ alkyl optionally substituted by fluoro; and
R$^2$ is C$_2$–C$_4$ alkyl.

2. A compound as claimed in claim 1 wherein R is —CO$_2$H.

3. A compound as claimed in claim 1 or 2 wherein R$^1$ is C$_3$–C$_8$ alkyl.

4. A compound as claimed in claim 3 wherein R$^1$ is C$_3$–C$_6$ alkyl and R$^2$ is C$_2$–C$_3$ alkyl.

5. A compound as claimed in claim 4 wherein R$^1$ is n-propyl, n-butyl, n-pentyl or n-hexyl, and R$^2$ is ethyl or n-propyl.

6. A compound as claimed in claim 1 which is 4-(3-[(2-n-butyl-2-[4-ethyl]phenyl-1,3-benzodioxolan-5-yl) methylcarbonyl]indol-1-yl)butanoic acid or 4-(3-[(2-n-butyl-2-[4-n-propyl]phenyl-1,3- benzodioxolan-5-yl) methylcarbonyl]indol-1-yl)butanoic acid, or a pharmaceutically acceptable base salt thereof.

7. A pharmaceutical composition comprising an effective amount of a compound of the formula (I), or a pharmaceutically acceptable base salt thereof, as claimed in claim 1, together with a pharmaceutically acceptable diluent or carrier.

8. A compound as claimed in claim 5, wherein R$^1$ is n-butyl.

* * * * *